United States Patent [19]

Wills

[11] Patent Number: 4,646,000

[45] Date of Patent: Feb. 24, 1987

[54] METHOD AND APPARATUS FOR MEASURING SOIL SALINITY

[75] Inventor: Robert H. Wills, Ely, Vt.

[73] Assignee: The Yellow Springs Instrument Company, Yellow Springs, Ohio

[21] Appl. No.: 669,693

[22] Filed: Nov. 8, 1984

[51] Int. Cl.[4] .......................................... G01R 27/26
[52] U.S. Cl. ................... 324/61 R; 324/376; 324/444
[58] Field of Search ............... 204/1 A, 1 B, 1 T, 406; 324/355, 354, 376, 442, 444, 61 R, 60 R, 60 C

[56] References Cited

U.S. PATENT DOCUMENTS

| | | |
|---|---|---|
| 2,076,441 | 4/1937 | Berry . |
| 2,942,176 | 6/1960 | Brownscombe ................... 324/376 |
| 3,448,381 | 6/1969 | Perry . |
| 3,500,182 | 3/1970 | Reed et al. . |
| 3,501,692 | 3/1970 | Kluck . |
| 3,713,022 | 1/1973 | McRay ............................. 324/60 C |
| 3,720,890 | 3/1973 | Anderson . |
| 3,782,179 | 1/1974 | Richards . |
| 3,959,723 | 5/1976 | Wagner . |
| 4,070,612 | 1/1978 | McNeill et al. . |
| 4,181,881 | 1/1980 | Preikschat ........................ 324/61 R |
| 4,236,109 | 11/1980 | Ingle, Jr. . |
| 4,319,185 | 3/1982 | Hill . |
| 4,322,678 | 3/1982 | Capots ............................. 324/61 R |
| 4,341,112 | 7/1982 | Mackay et al. . |
| 4,364,008 | 12/1982 | Jacques . |

FOREIGN PATENT DOCUMENTS

| | | | |
|---|---|---|---|
| 0282113 | 10/1966 | Australia ........................... 324/333 |
| 1057833 | 11/1983 | U.S.S.R. .......................... 324/61 R |

OTHER PUBLICATIONS

Benin: "A Frequency Dielectric Method of Determining Salt Contents . . . ", Measurement Techniques–Oct. 74–pp. 1589–1592.
Topp: "Electromagnetic Determination of Soil Water Content . . . "–Water Resources Research–vol. 16, No. 3, pp. 574–582, Jun. 1980.
Chernyak: "Dielectric Methods for Investigating Moist Soils"–Geological Committee of the USSR, (VSEGINGEO)–1964.
Wait: "Note on Determining Electrical Ground Constants . . . ", J. Appl. Physics.–vol. 43, No. 3, Mar. 1972.
Rhoades: "Monitoring Soil Salinity . . . ", American Water Resources Asso.–1978 Symposium–Jun. 12, 1978.

Primary Examiner—Reinhard J. Eisenzopf
Assistant Examiner—Jose M. Solis
Attorney, Agent, or Firm—Biebel, French & Nauman

[57] ABSTRACT

A method for measuring soil salinity measures the low frequency permittivity of a soil sample at one or more frequencies below 2 megahertz and determines the salinity of the soil sample based on the measured real part of the permittivity. Apparatus for performing the method comprises a soil sample holder for laboratory measurements or a four electrode array for measuring soil salinity in situ. An electrical circuit measures the low frequency permittivity of the soil sample and converts the measured permittivity to the salinity of the soil sample. The salinity conversion can be performed by a read-only memory or a computer with the output being registered by display on a digital or analog display or storage in a data memory.

15 Claims, 4 Drawing Figures

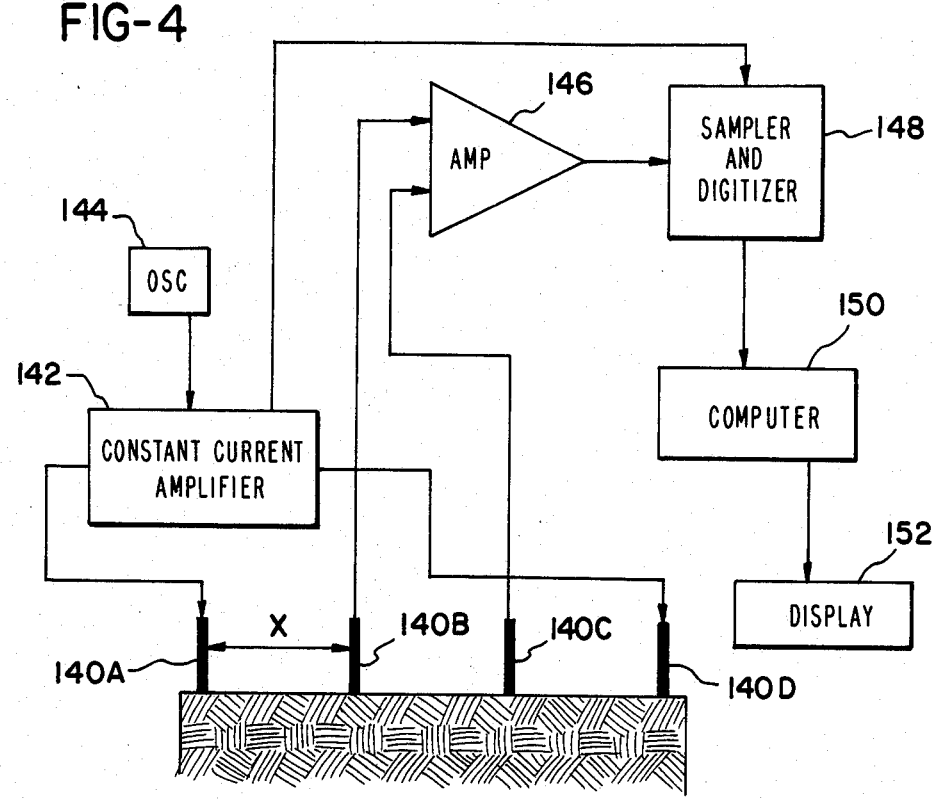

METHOD AND APPARATUS FOR MEASURING SOIL SALINITY

BACKGROUND OF THE INVENTION

The present invention relates generally to measuring characteristics of soil and, more particularly, to a method and apparatus for determining the salinity or salt content of soil.

The salinization of soil is generally caused over time by the transportation of small quantities of inorganic salts into the soil by irrigation water. As the irrigation water evaporates and is transpired, the salts are left behind and may accumulate to cause damage to plant life unless sufficient irrigation water is provided to leach the salt to below the root zone of plants occupying the soil.

High levels of irrigation unfortunately may not be a solution to soil salinity problems even if unlimited amounts of water are available. Upward capillary transport and evaporation of saline ground water causes a high salt concentration just above the water table. Over irrigation may raise the water table bringing the high salinity region into the root zone of plants occupying the soil. Thus, it can be seen that soil salinity measuring devices are needed to gauge the extent of salinity problems, to monitor changes in soil salinity level over time, and to provide a guide to optimizing crop yields and preserving or reclaiming agricultural lands which may be threatened by salinity problems.

The standard method of measuring soil salinity is to form a saturated paste by adding water to a soil sample and then extracting the soil pore water using vacuum filtration. This is described in detail in the USDA Handbook 60, 1954, "Diagnosis and Improvement of Saline and Alkali Soils." The salinity of the soil pore water extracted is gauged by its electrical conductivity. Saturation water content is used because it is repeatable and is the lowest practical water content for extraction purposes. Unfortunately, the extraction method for determining soil salinity is time consuming and is limited to performance in a laboratory.

As an alternative to the extraction of soil pore water from saturated pastes of soil samples, soil pore water may be collected by means of vacuum extractors which are placed in the field for in situ soil water sampling. Unfortunately, such in situ sampling is influenced by sampler in-take rate, plugging and sampler depth and size such that serious doubts remain about the representativeness of water samples collected by in situ extraction.

Another approach to in situ salinity monitoring has been buried porous salinity sensors which imbibe and come to diffusional equilibrium with the soil water. Unfortunately, such sensors have long response times which may be several days and are not accurate in dry soils.

Soil salinity can also be determined by measuring soil water electrical conductivity using four electrode or Wenner arrays and electrical measuring equipment. Unfortunately, the electrical conductivity of bulk soils is greatly effected by the soil type, as well as by salt and water contents.

While one or a combination of these known salinity measuring arrangements may be used for a given application, new alternatives for quickly and inexpensively measuring soil salinity are in demand and serve to advance the art of soil salinity measurement to facilitate soil studies and soil conservation.

SUMMARY OF THE INVENTION

In accordance with the present invention, soil salinity is determined as a function of low frequency electrical permittivity of the soil. As used herein, low frequency permittivity is also known and more accurately referred to as the real part of the permittivity which, in general, is a complex number. Applicant has recognized that the electrical permittivity of soil measured at one or more frequencies below 2 megahertz is related to the salinity of the soil represented by the soil extract conductivity. In the past, soil conductivity or bulk soil conductivity has been related to extract conductivity to measure soil salinity. Applicant has further determined that the relationship between low frequency electrical permittivity of soil to extract conductivity is less dependent upon other factors such as soil type and water content than is the relationship between soil conductivity and extract conductivity.

Although it is not entirely clear why this is the case, applicant believes that the difference is due to the different processes involved. Bulk soil conductivity is a measure of the ease of flow of salt ions through the irregular, unordered and circuitous path from one soil pore to another. Alternatively, low frequency electrical permittivity is effected by the bunching of ions within pores, which effect is known as interfacial dispersion. The bunching of ions within soil pores is less dependent upon soil type than is the flow of ions from pore-to-pore.

Applying applicant's recognition, a method for measuring soil salinity in accordance with the present invention comprises measuring the real part of the low frequency permittivity ($\epsilon'$) of the soil sample, i.e., at one or more frequencies below 2 megahertz, determining the salinity of the soil sample based on the measured real part of the permittivity, and registering the salinity of the soil sample. The moisture content of the soil sample may also be measured and used in the step of determining the salinity of the soil sample. the registration of the salinity of the soil sample may be by means of displaying the salinity on an appropriate analogue or digital display device or by storing the determined salinity in an appropriate data store. The soil type may also be used within the step of determining the salinity of the soil sample.

Apparatus for performing the method of measuring soil salinity in accordance with the present invention comprises sample means for engaging a soil sample, circuit means connected to the sample means for determining the real part of the low frequency permittivity of the soil sample and generating permittivity signals representative thereof, conversion means connected to the circuit means and responsive to the permittivity signals for generating salinity signals representative of the salinity of the soil sample, and salinity registration means for registering the salinity of the soil sample in response to the salinity signals.

The circuit means may further provide for determining the moisture content of the soil sample and for generating moisture signals representative of the moisture content. In that event, the conversion means is further responsive to the moisture signals for generating the salinity signals. The conversion means may comprise a read-only memory or a computer, and the registration means may comprise a digital or analog display or a data store.

It is, therefore, an object of the present invention to provide improved methods and apparatus for measuring the salinity of soil based on the low frequency electrical permittivity of the soil sample.

Other objects and advantages of the invention will be apparent from the following description, the accompanying drawings, and the appended claims.

BRIEF DESCRIPTION OF THE DRAWINGS

FIGS. 3 and 4 are block diagrams of two embodiments of apparatus for measuring the salinity of soil in situ.

DETAILED DESCRIPTION OF THE INVENTION

Figure 1:
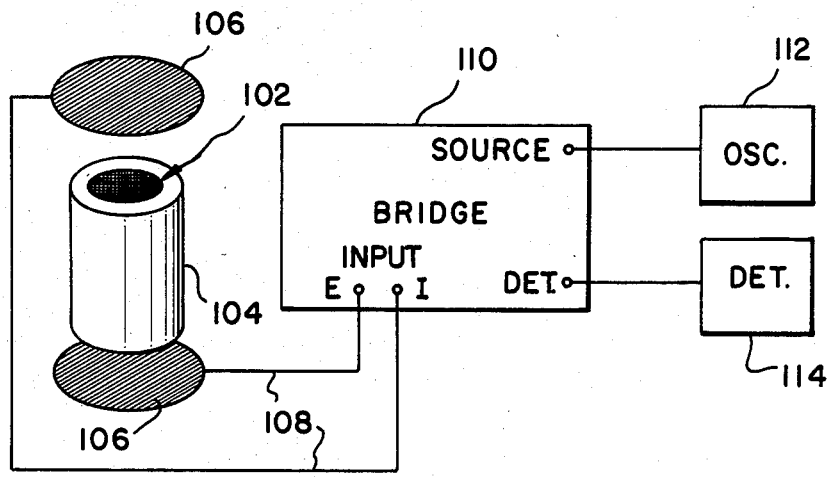
FIG. 1 is a block diagram of apparatus for performing a method in accordance with the present invention on a soil sample.

FIG. 1 is a block diagram of apparatus in accordance with the present invention which was utilized to determine soil salinity by measuring the real part of the low frequency electrical permittivity of soil. A soil sample 102 is packed into a plexiglass sleeve 104 and then clamped between plates 106 of a parallel plate sample holder, such as a Model D321 permittivity micrometer jig, available from Wayne Kerr. Conductors 108 extend from the plates 106 to a bridge circuit 110 to which the sample holder is connected as the unknown element.

In the apparatus of FIG. 1, the conductors 108 are connected to the E&I input terminals of a Wayne Kerr Model B221A universal impedence bridge. An oscillator circuit 112 is connected as the source or input for the bridge circuit 110 with a suitable oscillator being the Hewlett Packard Model 209A. Finally, a detector circuit 114 is connected to the detector output of the bridge circuit 110 with a suitable detector being the General Radio Model 1232A tuned detector. The identified instruments were selected since they were convenient in the laboratory in which the invention was made. It is to be noted that a large variety of instruments are available for interconnection as shown in FIG. 1.

To measure the low frequency electrical permittivity of the soil sample 102, the oscillator 112 is set to a desired frequency less than or equal to 2 megahertz and the detector circuit 114 is tuned for maximum response and sensitivity. The controls of the bridge circuit 110 are then rotated until a minimum detector reading or null is obtained. The conductance and capacitance of the sample 102 within the sleeve 104 are then read from the bridge circuit 110 and the electrical permittivity, i.e., the real part of the complex relative electric permittivity K or $\epsilon'$, calculated from the equation:

$$K = (C - C_0)L/A\epsilon_0$$

where K is the electrical permittivity, C is the measured capacitance of the sample in the sample holder, $C_0$ is the capacitance of the sample holder empty, A is the cross-sectional area of the sample holder, $\epsilon_0$ is the permittivity of free space, and L is the length of the sample holder, i.e., the sleeve 104.

Because the bridge circuit 110 utilized in the laboratory setup has a limited frequency range and to ensure the accuracy of the measurement of the water content of the samples, water content was measured by weighing, drying and then reweighing the samples in accordance with standard laboratory procedure.

It is noted that a less labor intensive arrangement can be constructed wherein the conductors 108 are directly connected to an impedence meter, such as a Hewlett Packard Model 4800A or 4815A. Here again, the desired frequency is selected and the value of the capacitance is read directly from a display on the meter. Calculation of the electrical permittivity is in accordance with the above equation. However, water content can be measured directly by making a high frequency electrical permittivity measurement, for example, at approximately 30 megahertz, by means of the equation:

$$\theta_v = 5.3 \times 10^{-2} + 2.92 \times 10^{-2} K_{hf} - 5.5 \times 10^{-4} K_{hf}^2 + 4.3 \times 10^{-6} K_{hf}^3$$

which is an empirical relationship developed by Topp, Davis and Annan wherein $\theta_v$ is the volumetric water content and $K_{hf}$ is the high frequency permittivity of the sample. See "Electromagnetic Determination of Soil Water Content: Measurements in Coaxial Transmission Lines," by G. C. Topp, J. L. Davis and A. P. Annan, *Water Resources Research*, Vol. 16, No. 3, pages 574–582, June, 1980. Of course, water content can be determined by other field instruments, if desired, as is well known in the art.

Utilizing the apparatus of FIG. 1 and conventional moisture content measuring techniques, 12 samples of two soils were tested. The first soil, Post Mills Silty Sand, is a New England agricultural soil typical of the glacial tills found in the Eastern United States and the second soil, Fairbanks Silt, is an agricultural soil from Alaska typical of the river deposited silts of the Midwest and Western United States. Each sample was dried and sufficient amounts of sodium chloride solutions were added to the dry samples to produce salinities covering the range of the salinity scale and moisture contents of approximately 100%, 50% and 25% saturation.

Table I gives pertinent information for the 12 soil samples of each soil type, with samples 1-6 being at 50% saturation with increasing salinity, samples 7-9 at 100% saturation with increasing salinity and samples 10-12 being at 25% saturation with increasing salinity. The designations in Table 1 are as follows: $\theta_v$ is the volumetric water content in percent; $\theta_g$ is the gravimetric water content in percent; $EC_w$ is the approximate conductivity of added water in decisiemens per meter; %NaCl is the amount of salt in the added water in percent; $EC_{5:1}$ is the five-to-one soil extract conductivity in decisiemens per meter; $\sigma_e$ is the effective soil conductance at 1 KHz; $K_e$ is the effective electrical permittivity at 1 KHz; and $K/\sigma \times 1000$ is the ratio of permittivity to conductivity times 1000. The bulk soil permittivity versus extract conductivity for the twelve samples is plotted on a log/log scale in FIG. 2. Soil extract conductivity at five-to-one dilution ($EC_{5:1}$), rather than saturation water content, was used for the test to speed measurement and to allow usage of smaller soil samples. The oscillator frequency used to obtain the data of Table I was 1 KHz.

TABLE I

| # | $\theta_v$ | $\theta_g$ | $EC_w$ | % NaCl | $EC_{5:1}$ | $\sigma_e$ | $K_e$ | $K/\sigma \times 1000$ |
|---|---|---|---|---|---|---|---|---|
| Fairbanks Silt | | | | | | | | |
| 1 | 16.70 | 9.71 | 0 | 0.0 | 11.5 | 7.65 | 2030 | 265.36 |
| 2 | 16.57 | 9.59 | 2 | 0.1 | 13.8 | 12.04 | 2310 | 191.86 |
| 3 | 17.13 | 9.58 | 4 | 0.2 | 15.7 | 16.56 | 3510 | 211.95 |
| 4 | 16.88 | 9.67 | 8 | 0.4 | 21.2 | 22.89 | 4330 | 189.16 |
| 5 | 16.27 | 9.57 | 16 | 0.9 | 31.5 | 36.54 | 6740 | 184.45 |
| 6 | 16.57 | 9.63 | 32 | 2.0 | 58.0 | 76.52 | 16000 | 209.09 |
| 7 | 39.37 | 20.09 | 0 | 0.0 | 10.6 | 18.54 | 2300 | 124.05 |
| 8 | 41.1 | 21.38 | 4 | 0.2 | 20.6 | 65.9 | 7720 | 118.60 |
| 9 | 39.13 | 20.14 | 16 | 0.9 | 57.7 | 183.6 | 58200 | 316.99 |
| 10 | 7.27 | 4.45 | 0 | 0.0 | 10.5 | 3.77 | 568 | 150.66 |
| 11 | 7.70 | 4.77 | 4 | 0.2 | 13.3 | 6.01 | 954 | 158.73 |
| 12 | 6.72 | 4.16 | 16 | 0.9 | 20.0 | 10.52 | 956 | 90.87 |
| Post Mills Silty Sand | | | | | | | | |
| 1 | 33.58 | 19.70 | 0 | 0.0 | 31.3 | 16.94 | 4820 | 284.53 |
| 2 | 35.74 | 19.26 | 2 | 0.1 | 30.2 | 32.75 | 6740 | 205.80 |
| 3 | 35.43 | 18.94 | 4 | 0.2 | 38.0 | 39.96 | 7710 | 192.94 |
| 4 | 35.06 | 18.68 | 8 | 0.4 | 42.5 | 64.92 | 14500 | 223.35 |
| 5 | 34.63 | 19.66 | 10 | 0.9 | 71.4 | 105.20 | 37300 | 354.56 |
| 6 | 35.37 | 18.76 | 32 | 2.0 | 116.0 | 242.30 | 101000 | 416.84 |
| 7 | 46.03 | 25.56 | 0 | 0.0 | 34.1 | 25.51 | 6710 | 263.03 |
| 8 | 46.33 | 26.34 | 4 | 0.2 | 46.3 | 66.98 | 12900 | 192.59 |
| 9 | 43.99 | 23.96 | 16 | 0.9 | 81.2 | 176.70 | 58800 | 332.76 |
| 10 | 16.02 | 9.79 | 0 | 0.0 | 25.9 | 4.37 | 1370 | 313.50 |
| 11 | 15.16 | 9.62 | 4 | 0.2 | 29.9 | 5.99 | 3240 | 540.90 |
| 12 | 14.73 | 9.48 | 16 | 0.9 | 43.9 | 13.84 | 5100 | 368.49 |

Figure 2:
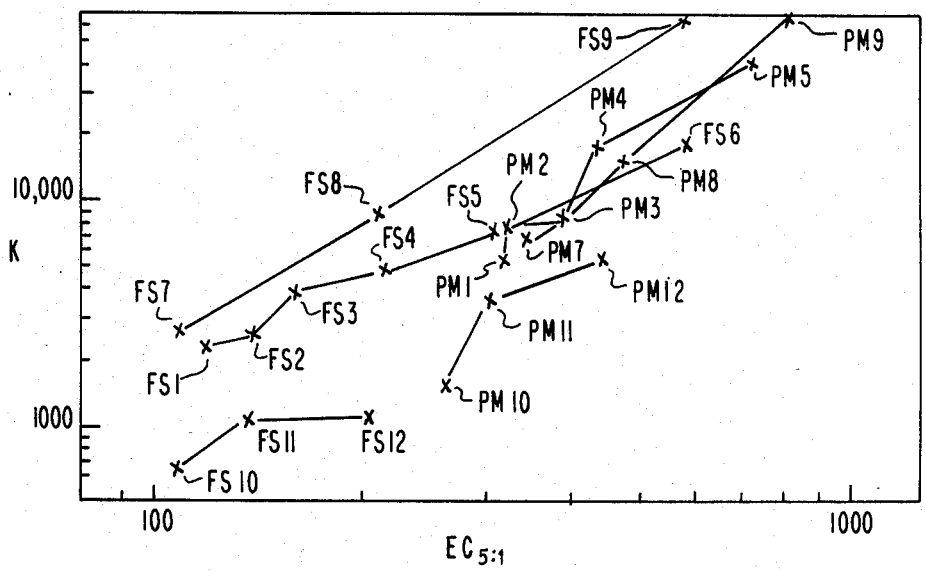
FIG. 2 is a graph of data generated in part by the apparatus of FIG. 1 and shown in Table I.

The relationship between the electrical permittivity and the extract conductivity or salinity of a soil sample as determined by the measurements made on the samples represented by Table I and FIG. 2 can be reduced to the following equations:

$$ln(EC_{5:1}) = m\,ln(K) + c$$

or $$EC_{5:1} = e^{(m\,ln(K)+c)}$$

or $$EC_{5:1} = e^c(K^m)$$

These equations mathematically describe the lines shown on the log/log scale graph of FIG. 2. The letters m and c indicate constants which have been calculated for each of the individual sets of samples with the same soil type and water content as shown in Table II.

TABLE II

| Soil Type | Water Content | Slope (m) | Intercept (c) |
|---|---|---|---|
| Fairbanks | 40 | 0.523 | 0.628 |
| Silt | 16 | 0.785 | −1.222 |
|  | 7 | 0.850 | −0.736 |
| Post Mills | 46 | 0.395 | 2.375 |
| Silty Sand | 35 | 0.448 | 1.861 |
|  | 15 | 0.371 | 2.830 |

The constants m and c were obtained utilizing minimum least squares line fitting, i.e., linear regression, as is well known in the art and described, for example, in Chapter 2 of "Econometrics," by Wonnacott & Wonnacott, Wylie, 1979. It is noted that a straight line on log/log scales is the same as the power law relationship of the last equation indicated above for $EC_{5:1}$.

While constants have been calculated for the three differing water contents of the samples measured, an approximation could be made for a working instrument by applying the equation with the mid-range water content constants. This equation would provide a close approximation for a determination of the soil salinity in view of the log/log relationship of the electrical permittivity to the saturation extract conductivity or salinity of the sample. It may be desirable to evaluate other soil types and provide similar equations for a large number of soil types with the soil type being a variable for the field instrument. Alternately, a single equation may be acceptable for measuring relative salinity for all soil types. The best embodiment for exploiting the present invention remains to be determined by additional testing and evaluation.

The straight line model of the relationship between electrical permittivity and extract conductivity or salinity of a soil sample can be extended to include water content. For this extension, the equations take the following form:

$$EC_{5:1} = e^{(m_1 ln(K) + m_2 ln(\theta_v) + c)}$$

or equivalently in power law form:

$$EC_{5:1} = ln\, c\, k^{m_1} \theta_v^{m_2}$$

where $\theta_v$ is the volumetric water content and $m_1$, $m_2$ and c are constants dependent upon soil type. These extended equations were obtained by well known multiple regression techniques, see Wannacott and Wannacott, supra, Chapter 3, and the data compiled in Table I. The following values were found for the constants for the two types of soil utilized in the verification of the present invention.

Fairbanks Silt: $m_1 = 0.603$; $m_2 = -0.605$; and $c = 2.06$

Post Mills Silty Sand: $m_1 = 0.418$; $m_2 = -0.317$; and $c = 3.3$.

It can be seen that the constants vary relatively little between the two soil types in terms of the logarithmic salinity scale which supports applicant's determination that low frequency permittivity of soil has little dependence upon soil type.

Figure 3:
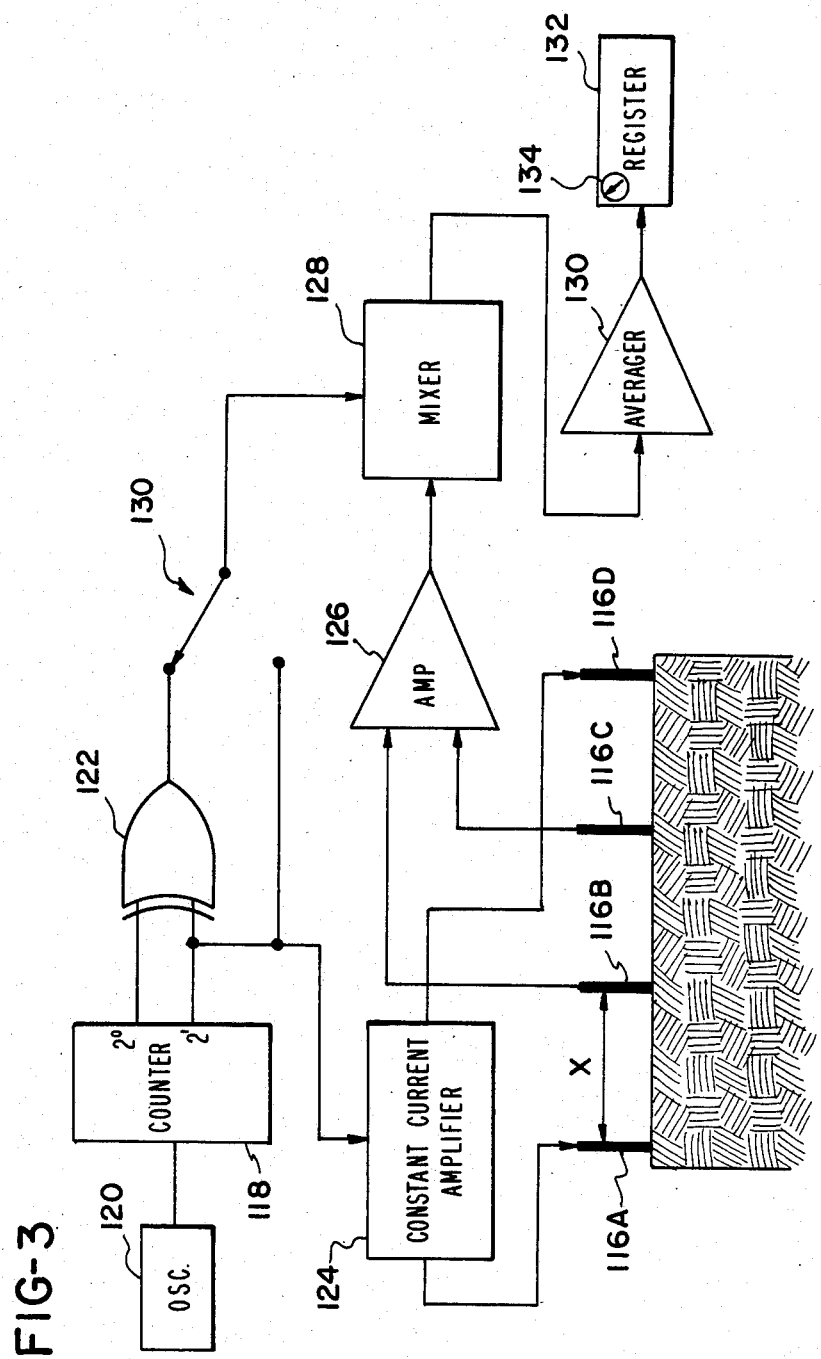

FIGS. 3 and 4 are block diagrams illustrating two embodiments of apparatus for measuring the salinity of soil in situ. In the illustrative embodiment of apparatus for the field measurement of soil salinity, four in-line electrodes are inserted into the ground to form a Wenner array. The electrodes are spaced equidistances X from one another.

In FIG. 3, the two outer electrodes 116A and 116D are driven by a square wave constant current source derived from a four state counter circuit 118. A square wave oscillator 120 generates a clock or count signal which is passed to the counter circuit 118. The $2^0$ and $2^1$ outputs of the counter circuit 118 are connected to an exclusive OR gate 122 and the $2^1$ output is connected to the input of a constant current amplifier 124 the output of which is connected to the outer electrodes 116A and 116D of the Wenner array 116 to provide the constant current square wave signal to those electrodes.

The inner electrodes 116B and 116C are connected to the inputs of an amplifier 126, the output of which is passed to a mixer circuit 128. The mixer circuit 128 is also driven by either the $2^1$ output signal from the counter circuit 118 or the output signal of the exclusive OR gate 122 dependent upon the positioning of a control switch 130. The output of the mixer circuit 128 is passed to an averaging circuit 130 which acts as a synchronous demodulator for the signal from the mixer circuit 128.

When the control switch 130 is connected to the $2^1$ output of the counter circuit 118, the output signal from the averaging circuit 130 is proportional to the in-phase portion of the voltage across the inner electrodes 116B and 116C of the Wenner array. This in-phase voltage signal is representative of soil conductivity $\sigma$ in accordance with the equation:

$$\sigma = I/(2\pi XV),$$

where I equals the current injected at the outer Wenner array electrodes 116A and 116D, V equals the voltage across the inner Wenner electrodes 116B and 116C and X equals the interelectrode spacing between the equally spaced electrodes 116 of the Wenner array.

When the control switch 130 is connected to the output of the exclusive OR gate 122, the mixer circuit 128 samples the interelectrode voltage at the output of the amplifier circuit 126 which is 90° out of phase with the current applied to the outer electrodes 116A and 116D. Accordingly, the output signal of the averaging circuit 130 is proportional to the permittivity of the soil sample engaged by the Wenner array 116. The permittivity is represented by the equation:

$$K = I/(4\pi^2 fXV)$$

where I equals the current injected at the outer Wenner electrodes 116A and 116D, V equals the voltage generated across the inner Wenner electrodes 116B and 116C, X equals the interelectrode spacing and f equals the frequency of the injected current. This equation is derived from the relationship between the capacitance C and the capacitive reactance $X_c$:

$$C = 1/(2\pi f X_c).$$

The output signal of the averaging circuit 130 is passed to a register circuit 132 which may include a meter 134 or other analog or digital display device for showing the conductivity or the permittivity being measured by the device. The register 132 may include storage means for storing the signals representative of the conductivity and the permittivity together with means for generating a salinity measurement based on the two signals such that the salinity is displayed by means of the meter 134 or other display device.

The permittivity signals or the permittivity signals and conductivity signals may be applied to the equations given above for the determination of the salinity of the soil sample into which the Wenner array has been inserted by means of preprogrammed read-only memories addressed by the two signals, a microcomputer or other well known arrangements which will be readily apparent to those skilled in the art of signal handling and data processing.

By operating the apparatus shown in FIG. 3, at two frequencies, both soil water content and salinity may be measured in situ. For example, a low frequency of about 1000 Hz may be used to measure the low frequency electrical permittivity and so the soil salinity and a high frequency of about 30 megahertz may be used to measure the high frequency permittivity and so the water content using the Topp, Davis and Annan relationship given above.

This method may encounter difficulties as stray capacitance in the electrodes and cables could cause problems at the high frequency. Alternatively, a lower frequency signal could be utilized, for example, 2 megahertz, and a mathematical model of the soil electrical permittivity generated to calculate the true high frequency permittivity, such as at 30 megahertz, from the 2 megahertz measurement. The 2 megahertz measurement contains elements of both the low frequency electrical permittivity representative of the soil salinity and the high frequency permittivity representative of the soil water content.

In the illustrative embodiment of field apparatus as shown in FIG. 4, permittivity and conductivity data over a range of frequencies are available by means of time domain measurements. Outer electrodes 140A and 140D of a Wenner array are driven by a constant current square wave source comprising a constant current amplifier 142 and a square wave oscillator 144 in a manner similar to that of the embodiment of FIG. 3. The voltage across the inner electrodes 140B and 140C are amplified by an amplifier circuit 146 and in turn passed to a sampler and digitizer circuit 148.

The current signal driving the outer electrodes 140A and 140D of the Wenner array are similarly passed to the sample and digitizer circuit 148. Two time series are generated by the sampler and digitizer circuit 148 representative of the drive current on the outer electrodes 140A and 140D and the corresponding voltage generated across the inner electrodes 140B and 140C and are passed to a computer 150 wherein a Fourier transformation is applied to determine impedance data at the fundamental frequency and at harmonics of the fundamental frequency of the square wave signal generated by the oscillator 144. The salinity calibration equations, Topp et al.'s water content equation and a model of permittivity versus frequency, if necessary, can then be incorporated into the computer 150 to calculate salinity and water content of a soil sample engaged by the Wenner array 140 which are then passed to a display circuit 152.

The present invention can also be embodied in noninvasive apparatus for measuring soil salinity. For example, low frequency electrical permittivity can be measured by electromagnetic induction wherein an electrical current is induced in the ground from a loop of wire lying on the surface of the ground or supported thereabove, with the field resulting from the induced currents being sensed in either a second or the same loop. Electrical permittivity can be sensed at frequencies around 2 megahertz and soil water content can be sensed at anywhere from the 2 megahertz range to the higher frequencies. The theory of electromagnetic induction over a layered ground is well known in the art. While this theory has been limited to resistivity measurements, it should be easily expandable in accordance with the teachings of the present application to measuring electrical permittivity.

While the methods herein described and the forms of apparatus for carrying these methods into effect constitute preferred embodiments of this invention, it is to be understood that the invention is not limited to these precise methods and forms of apparatus and that changes may be made in either without departing from the scope of the invention which is defined in the appended claims.

What is claimed is:

1. A method for measuring soil salinity comprising the following steps:
   measuring the real part of the low frequency electric permittivity ($\epsilon'$) of a soil sample;
   determining the salinity of said soil sample based on the measured real part of the low frequency electric permittivity ($\epsilon'$); and
   registering the salinity of said soil sample.

2. A method for measuring soil salinity as claimed in claim 1 wherein the step of measuring the low frequency electric permittivity is performed at one or more frequencies below 2 megahertz.

3. A method for measuring soil salinity as claimed in claim 2 further comprising the step of measuring the moisture content of said soil sample and wherein the step of determining the salinity of said soil sample is based on the measured electric permittivity and the measured moisture content of said soil sample.

4. A method of measuring soil salinity as claimed in claim 3 further comprising determining the soil type wherein the step of determining the salinity of said soil sample comprises calculating the extract conductivity based on the soil type, measured electric permittivity and measured moisture content of said soil sample.

5. A method for measuring soil salinity as claimed in claim 4 wherein the step of registering the salinity of said soil sample comprises displaying the determined salinity.

6. A method for measuring soil salinity as claimed in claim 4 wherein the step of registering the salinity of said soil sample comprises storing the determined salinity.

7. Apparatus for measuring soil salinity comprising:
   sample means for engaging a soil sample the salinity of which is to be determined;
   circuit means connected to said sample means for measuring the real part of the low frequency electric permittivity ($\epsilon'$) of said soil sample and for generating electric permittivity signals representative thereof;
   conversion means connected to said circuit means and responsive to said permittivity signals for generating salinity signals representative of the salinity of said soil sample; and
   salinity registration means for registering the salinity of said soil sample in response to said salinity signals.

8. Apparatus as claimed in claim 7 wherein said low frequency electric permittivity is determined at one or more frequencies at or below 2 megahertz.

9. Apparatus as claimed in claim 8 wherein said conversion means is further responsive to moisture signals representative of the moisture content of said soil sample for generating said salinity signals.

10. Apparatus as claimed in claim 9 wherein said moisture signals are generated by the operator of said apparatus.

11. Apparatus as claimed in claim 9 wherein said circuit means further provides for measuring the moisture content of said soil sample and generating said moisture signals.

12. Apparatus as claimed in claim 9 wherein said conversion means comprises a read-only memory.

13. Apparatus as claimed in claim 9 wherein said conversion means comprises a computer.

14. Apparatus as claimed in claim 9 wherein said salinity registration means comprises a display.

15. Apparatus as claimed in claim 9 wherein said salinity registration means comprises a data store.

* * * * *